(12) United States Patent  (10) Patent No.: US 8,261,745 B2
Chandran et al.  (45) Date of Patent: Sep. 11, 2012

(54) VENTILATION INTERFACE

(75) Inventors: Sanjay Chandran, Boca Raton, FL (US); Shara Hernandez, Davie, FL (US); Louis Javier Collazo, Atlanta, GA (US)

(73) Assignee: Respcare, Inc., Coconut Creek, FL (US)

( * ) Notice: Subject to any disclaimer, the term of this patent is extended or adjusted under 35 U.S.C. 154(b) by 709 days.

(21) Appl. No.: 11/298,679

(22) Filed: Dec. 12, 2005

(65) Prior Publication Data

US 2006/0174887 A1 Aug. 10, 2006

Related U.S. Application Data

(60) Provisional application No. 60/634,802, filed on Dec. 10, 2004, provisional application No. 60/645,672, filed on Jan. 21, 2005.

(51) Int. Cl.
*A62B 18/08* (2006.01)
(52) U.S. Cl. .......... 128/206.24; 128/206.21; 128/205.25
(58) Field of Classification Search ............ 128/205.25, 128/206.12, 206.21, 204.23, 206.14–18, 128/207.13, 206.24, 206.28, 206.27, 207.18
See application file for complete search history.

(56) References Cited

U.S. PATENT DOCUMENTS

| 443,191 | A | * | 12/1890 | Illing | 128/203.22 |
|---|---|---|---|---|---|
| 1,125,542 | A | | 1/1915 | Humphries | |
| 2,415,846 | A | * | 2/1947 | Randall | 128/206.24 |
| 2,433,565 | A | * | 12/1947 | Korman | 128/204.12 |
| 3,670,726 | A | | 6/1972 | Mahon et al. | |
| 3,739,774 | A | | 6/1973 | Gregory | |
| 3,754,552 | A | | 8/1973 | King | |
| 3,861,385 | A | | 1/1975 | Carden | |
| 3,902,486 | A | | 9/1975 | Guichard | |
| 3,905,361 | A | | 9/1975 | Hewson et al. | |
| 4,156,426 | A | | 5/1979 | Gold | |
| 4,248,218 | A | | 2/1981 | Fischer | |
| 4,267,845 | A | | 5/1981 | Robertson, Jr. et al. | |
| 4,273,124 | A | | 6/1981 | Zimmerman | |
| 4,312,359 | A | | 1/1982 | Olson | |
| 4,367,735 | A | | 1/1983 | Dali | |
| 4,367,816 | A | | 1/1983 | Wilkes | |
| 4,406,283 | A | | 9/1983 | Bir | |

(Continued)

FOREIGN PATENT DOCUMENTS

DE 146688 2/1981

(Continued)

OTHER PUBLICATIONS

Respironics Co.—Mask Family—http://masksfamily.respironics.com/ viewed on Apr. 20, 2007.

(Continued)

*Primary Examiner* — Steven Douglas
*Assistant Examiner* — Colin W Stuart
(74) *Attorney, Agent, or Firm* — Maier & Maier PLLC

(57) ABSTRACT

A respiration assist mask having an input gas feed tube, a ventilation interface, a facial interface and nasal inserts. The gas feed tube can connect to the ventilation interface and form a seal. The ventilation interface may be joined with the facial interface to form a seal between the ventilation interface and the facial interface, as well as between the facial interface and the face of a user. Additionally, nasal inserts may be inserted into a portion of the facial interface and form a seal between the inserts and the facial interface.

20 Claims, 7 Drawing Sheets

SECTION A-A

U.S. PATENT DOCUMENTS

| | | | |
|---|---|---|---|
| 4,414,973 A * | 11/1983 | Matheson et al. | 128/206.15 |
| 4,422,456 A | 12/1983 | Tiep | |
| 4,493,614 A | 1/1985 | Chu et al. | |
| 4,549,542 A | 10/1985 | Chien | |
| 4,587,967 A | 5/1986 | Chu et al. | |
| 4,601,465 A | 7/1986 | Roy | |
| 4,617,637 A | 10/1986 | Chu et al. | |
| 4,660,555 A | 4/1987 | Payton | |
| 4,699,139 A | 10/1987 | Marshall et al. | |
| 4,706,664 A | 11/1987 | Snook et al. | |
| 4,753,233 A | 6/1988 | Grimes | |
| 4,774,946 A | 10/1988 | Ackerman et al. | |
| 4,782,832 A | 11/1988 | Trimble et al. | |
| 4,899,740 A | 2/1990 | Napolitano | |
| 4,915,105 A | 4/1990 | Lee | |
| 4,996,983 A | 3/1991 | AmRhein | |
| 5,000,173 A | 3/1991 | Zalkin et al. | |
| 5,022,900 A | 6/1991 | Bar-Yona et al. | |
| 5,025,805 A | 6/1991 | Nutter | |
| 5,038,772 A | 8/1991 | Kolbe et al. | |
| 5,046,491 A | 9/1991 | Derrick | |
| 5,074,297 A | 12/1991 | Venegas | |
| 5,113,857 A | 5/1992 | Dickerman et al. | |
| 5,121,745 A | 6/1992 | Israel | |
| 5,127,397 A | 7/1992 | Kohnke | |
| 5,137,017 A | 8/1992 | Salter | |
| D333,015 S | 2/1993 | Farmer et al. | |
| 5,188,101 A | 2/1993 | Tumolo | |
| 5,243,971 A * | 9/1993 | Sullivan et al. | 128/205.25 |
| 5,265,592 A | 11/1993 | Beaussant | |
| 5,265,595 A | 11/1993 | Rudolph | |
| 5,269,296 A | 12/1993 | Landis | |
| 5,271,391 A | 12/1993 | Graves | |
| 5,299,599 A | 4/1994 | Farmer et al. | |
| 5,335,656 A | 8/1994 | Bowe et al. | |
| 5,355,893 A | 10/1994 | Mick et al. | |
| 5,372,130 A | 12/1994 | Stern et al. | |
| 5,375,593 A | 12/1994 | Press | |
| 5,385,141 A | 1/1995 | Granatiero | |
| 5,394,568 A | 3/1995 | Brostrom et al. | |
| 5,396,885 A | 3/1995 | Nelson | |
| 5,398,676 A | 3/1995 | Press et al. | |
| 5,400,776 A | 3/1995 | Bartholomew | |
| 5,425,359 A | 6/1995 | Liou | |
| 5,437,267 A | 8/1995 | Weinstein et al. | |
| 5,509,409 A | 4/1996 | Weatherholt | |
| 5,526,806 A | 6/1996 | Sansoni | |
| 5,533,506 A | 7/1996 | Wood | |
| 5,535,739 A * | 7/1996 | Rapoport et al. | 128/204.23 |
| 5,560,354 A | 10/1996 | Berthon-Jones et al. | |
| 5,682,881 A | 11/1997 | Winthrop et al. | |
| 5,740,799 A | 4/1998 | Nielsen | |
| 5,794,619 A | 8/1998 | Edelman et al. | |
| 5,906,203 A | 5/1999 | Klockseth et al. | |
| 5,954,049 A | 9/1999 | Foley et al. | |
| 6,082,360 A * | 7/2000 | Rudolph et al. | 128/206.25 |
| 6,123,071 A | 9/2000 | Berthon-Jones et al. | |
| 6,357,441 B1 | 3/2002 | Kwok et al. | |
| 6,405,729 B1 * | 6/2002 | Thornton | 128/848 |
| 6,431,172 B1 | 8/2002 | Bordewick | |
| 6,439,234 B1 | 8/2002 | Curti et al. | |
| 6,478,026 B1 | 11/2002 | Wood | |
| 6,561,188 B1 | 5/2003 | Ellis | |
| 6,561,193 B1 | 5/2003 | Noble | |
| 6,571,798 B1 | 6/2003 | Thornton | |
| 6,581,601 B2 | 6/2003 | Ziaee | |
| 6,581,602 B2 | 6/2003 | Kwok et al. | |
| 6,595,214 B1 | 7/2003 | Hecker et al. | |
| 6,595,215 B2 | 7/2003 | Wood | |
| 6,637,434 B2 | 10/2003 | Noble | |
| 6,644,315 B2 * | 11/2003 | Ziaee | 128/206.21 |
| 6,655,385 B1 | 12/2003 | Curti et al. | |
| D485,905 S | 1/2004 | Moore et al. | |
| 6,679,265 B2 | 1/2004 | Strickland et al. | |
| 6,766,800 B2 | 7/2004 | Chu et al. | |
| 6,926,004 B2 * | 8/2005 | Schumacher | 128/206.27 |
| 7,047,972 B2 * | 5/2006 | Ging et al. | 128/207.11 |
| 7,069,933 B2 * | 7/2006 | Kwok et al. | 128/206.24 |
| D550,836 S | 9/2007 | Chandran et al. | |
| 7,523,754 B2 * | 4/2009 | Lithgow et al. | 128/206.24 |
| 2002/0046755 A1 | 4/2002 | DeVoss | |
| 2002/0053347 A1 | 5/2002 | Ziaee | |
| 2002/0108613 A1 * | 8/2002 | Gunaratnam et al. | 128/205.25 |
| 2002/0124849 A1 | 9/2002 | Billette de Villemeur | |
| 2002/0174868 A1 * | 11/2002 | Kwok et al. | 128/205.25 |
| 2003/0019495 A1 * | 1/2003 | Palkon et al. | 128/206.21 |
| 2003/0079749 A1 | 5/2003 | Strickland et al. | |
| 2003/0172936 A1 * | 9/2003 | Wilkie et al. | 128/207.18 |
| 2003/0196658 A1 | 10/2003 | Ging et al. | |
| 2004/0112384 A1 | 6/2004 | Lithgow et al. | |
| 2005/0028822 A1 | 2/2005 | Sleeper et al. | |
| 2005/0033247 A1 | 2/2005 | Thompson | |
| 2005/0051176 A1 | 3/2005 | Riggins | |
| 2005/0061326 A1 | 3/2005 | Payne, Jr. | |
| 2006/0032504 A1 * | 2/2006 | Burton et al. | 128/207.11 |
| 2006/0124131 A1 | 6/2006 | Chandran et al. | |
| 2006/0137690 A1 | 6/2006 | Gunaratnam et al. | |
| 2006/0237017 A1 | 10/2006 | Davidson et al. | |
| 2006/0283461 A1 | 12/2006 | Lubke et al. | |
| 2007/0144525 A1 | 6/2007 | Davidson et al. | |
| 2007/0272249 A1 | 11/2007 | Chandran et al. | |
| 2008/0006277 A1 | 1/2008 | Worboys et al. | |

FOREIGN PATENT DOCUMENTS

| | | | |
|---|---|---|---|
| DE | 19944242 | | 3/1991 |
| DE | 3719009 | | 12/1998 |
| EP | 93309991.3 | | 6/1995 |
| GB | 0532214 | | 1/1941 |
| GB | 2368533 | | 5/2002 |
| WO | WO 01/97892 | A1 | 6/2000 |
| WO | PCT/AU2004/001832 | | 7/2005 |
| WO | WO 2005063328 | A1 * | 7/2005 |
| WO | WO 2008/040050 | A1 | 4/2008 |

OTHER PUBLICATIONS

ResMed Co.—Mask Products—http://www.resmed.com/en-us/products/product-catalog.html?menu=products viewed on Apr. 20, 2007.

Fisher and Paykel Co.—Product Family—http://www.fphcare.com/osa/products.asp viewed on Apr. 20, 2007.

Hans Rudolph Inc.—Mask Products—http://www.rudolphkc.com/products.php?category=MASKS viewed on Apr. 20, 2007.

Snapp Nasal Interface, Tiara Medical Systems, Inc. http://www.tiaramed.com/asp_shop/shopdisplayproducts.asp?id=109&cat=SNAPP%2A+Nasal+Interface, viewed May 17, 2005.

U.S. Appl. No. 60/533,214, filed Dec. 2004.

* cited by examiner

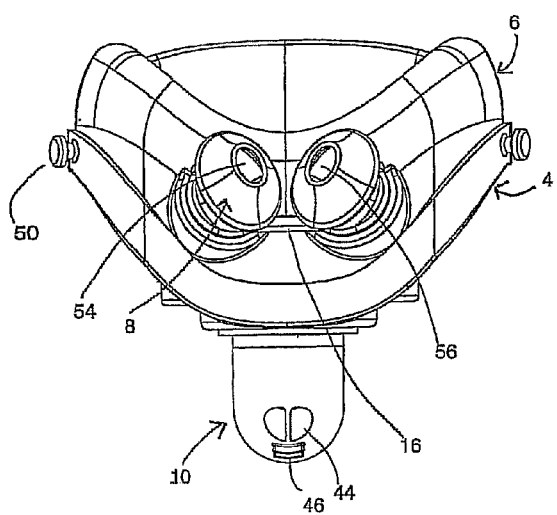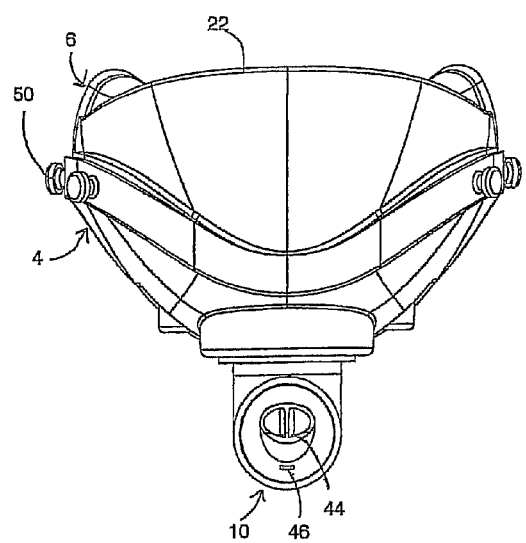
Figure 5
Figure 6

SECTION E-E

SECTION A-A

SECTION E-E

SECTION A-A

VENTILATION INTERFACE

PRIORITY CLAIM UNDER 35 U.S.C. §119

This invention is related to and claims priority under 35 U.S.C. §119 to both U.S. Provisional Patent Application 60/634,802, filed Dec. 10, 2004, and U.S. Provisional Patent Application 60/645,672, filed Jan. 21, 2005, and the contents of both are hereby incorporated in their entirety.

FIELD OF THE INVENTION

This invention relates generally to the field of respiration or breathing assist masks. In particular, the invention relates to respiration or breathing assist masks utilizing both the nose and mouth.

BACKGROUND

Obstructive sleep apnea syndrome (commonly referred to as obstructive sleep apnea, sleep apnea syndrome, and/or sleep apnea) is a medical condition that includes repeated, prolonged episodes of cessation of breathing during sleep. During a period of wakefulness, the muscles of the upper part of the throat passage of an individual keep the passage open, thereby permitting an adequate amount of oxygen to flow into the lungs. During sleep, the throat passage tends to narrow due to the relaxation of the muscles. In those individuals having a relatively normal-sized throat passage, the narrowed throat passage remains open enough to permit the adequate amount of oxygen to flow into the lungs. However, in those individuals having a relatively smaller-sized throat passage, the narrowed throat passage prohibits the adequate amount of oxygen from flowing into the lungs. Additionally, a nasal obstruction, such as a relatively large tongue, and/or certain shapes of the palate and/or the jaw of the individual, further prohibit the adequate amount of oxygen from flowing into the lungs.

An individual having the above-discussed conditions can stop breathing for one or more prolonged periods of time (e.g. ten seconds or more). The prolonged periods of time during which breathing is stopped, or apneas, are generally followed by sudden reflexive attempts to breathe. The reflexive attempts to breathe are generally accompanied by a change from a relatively deeper stage of sleep to a relatively lighter stage of sleep. As a result, the individual suffering from obstructive sleep apnea syndrome generally experiences fragmented sleep that is not restful. The fragmented sleep results in one or more of excessive and/or inappropriate daytime drowsiness, headache, weight gain or loss, limited attention span, memory loss, poor judgment, personality changes, lethargy, inability to maintain concentration, and/or depression.

Other medical conditions can also prevent individuals, including adults and infants, from receiving the adequate amount of oxygen into the lungs. For example, an infant who is born prematurely can have lungs that are not developed to an extent necessary to receive the adequate amount of oxygen. Further, prior to, during and/or subsequent to certain medical procedures and/or medical treatments, an individual can be unable to receive the adequate amount of oxygen. Under these circumstances, it is known to use a ventilation interface to apply a positive pressure to the throat of the individual, thereby permitting the adequate amount of oxygen to flow into the lungs. In the known ventilation interface, oxygen and/or room air containing oxygen is delivered through the mouth and/or nose of the individual. Existing types of positive pressure applied by the known ventilation interface include continuous positive airway pressure (CPAP), in which a positive pressure is maintained in the throat passage throughout a respiratory cycle, bi-level positive airway pressure (BiPAP), in which a relatively high positive pressure is maintained during inspiration and a relatively low positive pressure is maintained during expiration, and intermittent mechanical positive pressure ventilation (IPPV) in which a positive pressure is applied when apnea is sensed (i.e., the positive airway pressure is applied intermittently or non-continuously).

One conventional ventilation interface for the application of positive pressure includes a face mask that covers both the nose and the mouth. See, for example, U.S. Pat. No. 4,263,908 to Mizerak and U.S. Pat. No. 6,123,071 to Berthon-Jones et al. Other face masks include configurations that cover only the nose or only the mouth. Standard masks have air supplied under pressure and use headgear or harnesses configured at least with what is referred to as a lip strap, thereby preventing air from escaping from the user's mouth. Such a strap is positioned level the patient's lips and wasp circumferentially around the patient's head from one side of the mask to the other. To keep the supply of positive gas pressure and to maintain the required seal that prevents the gas supply from leaking, a force must be applied to the head of the individual. As a result, the harness is generally uncomfortable to wear, particularly when sleeping. The applied pressure often results in undesirable irritation and sores caused by movement of the mask and harness during periods of both wakefulness and sleep. Further, the required seal is generally difficult to maintain when the mask and harness is moved.

The force that the harness applied to the mask against the face also applies an undesirable pressure to the sinus area adjacent to the nose, causing the nasal sinus airways to narrow. This narrowing causes an increase in the velocity of flow through the upper anatomical airways and a decrease in the lateral pressure against the nasal mucosal wall. Additionally, if the tubing between the mask and the gas supply unit folds undesirably, this problem will be exacerbated. The above-discussed combination of increased flow velocity and decreased pressure results in the removal of moisture form the mucosal walls during inspiration and may cause an undesirable drying and a burning sensation within the nares. As a result, the individual may remove the mask to alleviate these discomforts, consequently discontinuing the beneficial application of the positive pressure. Such increased air flow velocity and decreased pressure deteriorate the laminar flow between the air input and output portions of the conventional mask.

A common complaint of a patient regarding ventilation masks is that they cause claustrophobia. Such masks have large headgear that wrap around the entirety of the user's head and cover a significant area of the face including the periphery of both the nose and the mouth. Additionally such masks have a large amount of dead space within the mask where gas can be re-breathed by a patient, and a large area against the face of a user that must be sealed against the mask.

SUMMARY

In one embodiment, a ventilation mask is disclosed. The ventilation interface may have an outer face that can receive a gas supply tube. Additionally, the ventilation interface may have a cushioned facial interface that may connect to the outer face and create a seal therebetween. Further, at least one nasal insert may be removably fitted to the cushioned facial interface. A seal may be created between the at least one nasal insert and the cushioned facial interface. A seal may also be created between the at least one nasal insert and the nares of a user who is wearing the ventilation interface. Further, each of the components of the ventilation mask may be removed and replaced with other components of different sizes or shapes.

In another embodiment of the invention, a ventilation interface mask is disclosed having a gas supply tube, a front face, a cushioned interface connector and a least one nasal insert. The gas supply tube may be removably connected to the front face and to create a seal therebetween. The cushioned interface connector may be removably connected to the front face to create a seal therebetween. Additionally, the at least one nasal insert may be removably connected to the cushioned interface connector to create a seal therebetween.

BRIEF DESCRIPTION OF THE DRAWINGS

FIG. 5 shows a top view of an exemplary embodiment of the invention.

FIG. 6 shows a bottom view of an exemplary embodiment of the invention.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

Generally referring to FIGS. 1-8, a ventilation interface mask is disclosed. The interface may be used for a variety of purposes, for example providing continuous positive airway pressure to a user. The ventilation interface may alleviate concerns some users have by being small than other types of ventilation masks and by eliminating portions of the mask that fit over the nose of a user. Additionally, by eliminating the portions of a mask that fit over the nose of a user, less sealing is required against the face of a user. Also, the small size of the ventilation interface reduces the amount of space on the interior of the mask, thus resulting in less gas to exhaust and a decreased amount of gas that is breathed more than once.

Figure 1:
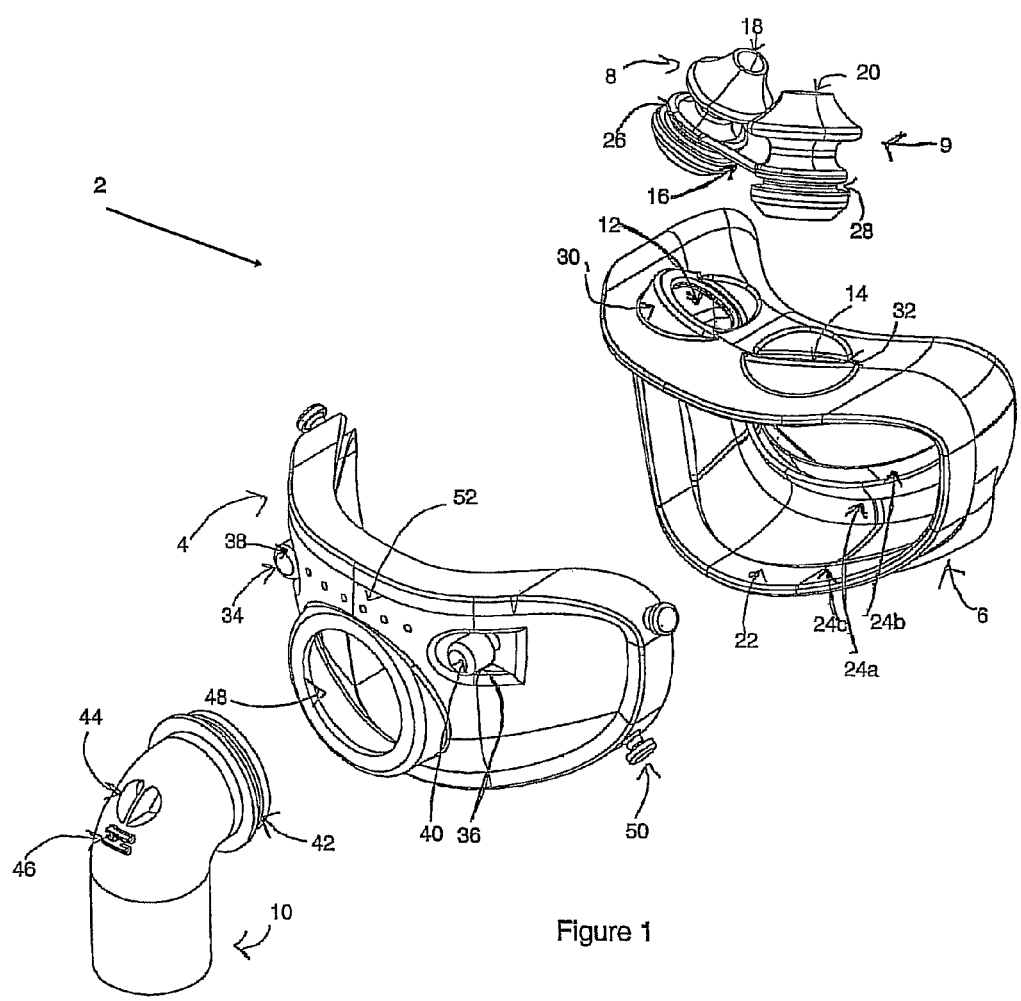
FIG. 1 shows an exploded view of an exemplary embodiment of the invention.

FIG. 1 shows an exploded view of an exemplary embodiment of a respiration assist mask. Respiration assist mask 2 may have several separable components, such as ventilation interface 4, cushioned facial interface 6, nasal inserts 8 and 9, and gas supply tube 10. In one embodiment of the invention, supply tube 10 may be connected to ventilation interface 4 in order for input gas may be supplied to the device. In a further embodiment, facial interface 6 may be joined with ventilation interface 4. Ventilation interface 4 may also accept nasal inserts 8 through receiving holes 12 and 14. The respiration assist mask 2 may then be positioned over the mouth of a user such that facial interface 6 forms an airtight seal over the mouth of the user. Additionally, in a further embodiment, facial interface 6 may form a seal against the upper and lower lips of the user. When respiration assist mask 2 is positioned over the mouth of a user, the user may insert nasal inserts 8 and 9 into the nares of a user. When nasal inserts 8 and 9 are inserted into the nares of a user, an airtight seal may be formed.

In another exemplary embodiment, nasal inserts 8 and 9 may be formed in a variety of shapes, for example the volcano style shown in FIG. 1. Additionally, any size or shape nasal insert that fits into the nares of a user and optionally provides an airtight seal may be used with respiration assist mask 2. Nasal inserts may be formed from any suitable material, for example silicone. In a further embodiment, nasal inserts 8 and 9 may be connected by connector 16. Connector 16 may be formed out of any material and is, optionally, formed out of the same material as the nasal inserts. Connector 16 can also be separable from nasal inserts 8 and 9, or, in a different embodiment, nasal inserts 8 and 9 can be formed without a connector. If connector 16 is fitted to nasal inserts 8 and 9, it may function to prevent the rotation of nasal inserts 8 and 9 when they are engaged on facial interface 6 in receiving holes 12 and 14, respectively. Additionally, connector 16 may act to retain nasal inserts 8 and 9 in a desired position. Alternatively, connector 16 may be removed to allow for rotation of nasal inserts 8 and 9 in receiving holes 12 and 14, respectively. Further, if connector 16 is removed, two different size nasal inserts may used and attached to respiration assist mask 2 if it is needed or desired by a user.

In another embodiment shown in FIG. 1, nasal inserts 8 and 9 may be formed with elliptical distal ends 18 and 20, respectively. Elliptical ends 18 and 20 may be formed so as to provide comfortable and airtight seals within the nares of a user. Connector 16 may be positioned on nasal inserts 8 and 9 so as to hold nasal inserts 8 and 9 in a position which provides a comfortable and airtight seal in the nares of the user.

In yet another embodiment shown in FIG. 1, facial interface 6 may provide an airtight seal against the face of a user. Additionally, facial interface 6 may act as a cushion against the face of a user. Similar to the removable cushion disclosed in U.S. Pat. No. 6,595,214 (the '214 patent), which was incorporated by reference into Provisional U.S. Patent Application No. 60/634,802 to which priority is claimed, facial interface 6 may act as a removable cushion that attaches to a ventilation interface. Facial interface 6 may also act to form a seal against an upper and/or lower lip of a user.

Additionally, facial interface 6 may include chin flap 22. When respiration assist mask 2 is placed on the face of a user, chin flap 22 may be positioned under the chin of the user. In one embodiment, chin flap 22 may provide additional sealing against the face of a user. Additionally, in another embodiment, chin flap 22 may act to provide additional comfort for a user. In a further embodiment, chin flap 22 can act to limit the movement of the lower jaw of a user.

In yet a further embodiment shown in FIG. 1, facial interface 6 may have multiple membranes 24a, 24b and 24c (collectively membranes 24). Membranes 24 may serve to provide additional seals against the face of a user. For example, membranes 24, and specifically membrane 24a, may seal against an upper and/or lower lip of a user who is wearing respiration assist mask 2. In this exemplary embodiment, membrane 24a may be formed to be thinner than membrane 24b. Thus, membrane 24a can adhere to facial contours and fill small facial gaps as it can be a thin, flexible material. Additionally, membrane 24b may be thicker than membrane 24a to provide auxiliary sealing against the face of a user and provide structural support for the device. For example, membrane 24a may be made of any suitable material, for example silicone, and may be approximately 0.020" thick. Membrane 24b may also be made of any suitable material, for example silicone, and have a thickness of approximately 0.050". Still other parts of facial interface 6, for example 24c, may have a thickness of approximately 0.100". This thickness may extend around the periphery of that portion of the device.

Also, membranes 24 may work in conjunction with chin flap 22 to provide additional sealing capabilities. As stated previously, in one embodiment, chin flap 22 may act to limit the movement of the lower jaw of a user. In a further embodiment, chin flap 22 may have some elasticity which allows a user wearing respiration assist mask 2 to move their jaw and, for example, open their mouth. In the event of this happening, membrane 24a, which also may be elastic, may stretch upper portion of the lower jaw of the user, thus maintaining the seal between the interface and a wearer's face. Membrane 24b, which may also be elastic, may then stretch against the bottom portion of the mouth of the user, thus maintaining an airtight seal between facial interface 6 and the face of a user.

Moreover, in a further exemplary embodiment of the invention, movement of the lower jaw of a user will not break the airtight seal of respiration assist mask 2 against the face of a user or dislodge the nasal inserts which may be positioned against the nares of a user. In this embodiment, when the mouth of a user wearing the mask opens, chin flap 22 allows facial interface 6 to stretch. For example, if a user were to open their mouth, the lower jaw of the user would move against chin flap 22, but remain in contact with chin flap 22 as it stretches. Thus, when facial interface 6 stretches, membranes 24 remain sealed against the moving face of the user.

In another embodiment shown in FIG. 1, facial interface 6 may have contoured surfaces around receiving holes 12 and 14. These contoured surfaces may work in conjunction with flange 26 of nasal insert 8 and flange 28 of nasal insert 9. Contoured surface 30 and contoured surface 32 may act to hold nasal insert 8 and nasal insert 9, respectively, in a position that allows for an airtight seal to be formed between the nasal inserts and the nares of a user wearing respiration assist mask 2. Also, contoured surfaces 30 and 32 may act to provide an airtight seal between nasal inserts 8 and 9, respectively and facial interface 6. In a further embodiment, contoured surfaces 30 and 32 can act to angle nasal inserts 8 and 9, respectively, towards each other and thus orientate them to be better received into the nares of a user.

In another exemplary embodiment shown in FIG. 1, auxiliary ports 34 and 36 may be positioned on ventilation interface 4. Auxiliary ports 34 and 36 may be positioned on an upper portion of interface 4 and may project outwardly. Additionally, when they are not being otherwise utilized, auxiliary ports 34 and 36 may be capped with coverings 38 and 40, respectively. Auxiliary ports may be used, for example, to connect to outside devices for the purposes of measuring oxygen or carbon dioxide levels, pressure, or to connect to any other outside device to provide measurements, readings or additional inputs. Alternatively, auxiliary ports 34 and 36 may be utilized as exhaust ports to release gas from the interior portion of ventilation interface 4. Removable coverings 38 and 40 may act to prevent the release of gas from respiration assist mask 2 and maintain the airtight seal within the device when.

Ventilation interface 4 may also have a design such that it can accept and seal with cushioned facial interfaces of various sizes. In one exemplary embodiment, cushioned facial interface 6 may be made to have different size or shape cushions or have a different sealing area. Different size facial interfaces may maintain a similar size or shape membrane to connect with ventilation interface 4, however. In other embodiments, different size facial interfaces may be made out of a material that stretches, so as to allow for an airtight seal to be formed between varying sizes of facial interface and ventilation interface 4.

FIG. 1 also shows input gas tube 10, which may be formed in an elbow shape or any other shape which may attach to ventilation interface 4. Input gas tube may be used to deliver any type of gas or aerosol and may be used in any type of respiration application, such as CPAP or BiPAP applications. Input gas tube 10 may have connection portion 42 which can be used to connect input gas tube 10 to ventilation interface 4 through the use of receiving hole 48. Connection portion 42 may be threading, allowing input gas tube 10 to be screwed into receiving hole 48 or any other connection and sealing mechanism, such as a clip or a clasp. Input gas tube 10 may also have valve 44 disposed on its surface. Valve 44 may be coupled with a flap, held in place by connector 46, which is closed in an airtight seal when ventilation gas is being passed through input gas tube 10. However, if there is no gas being inputted through tube 10, the flap will open, allowing outside air to enter respiration assist mask 2.

In another embodiment of the invention, the device may be worn on the face of a user with any of a variety of types of headgear. The headgear may attach to respiration assist mask 2 through the use of headgear attachment posts 50. Attachment posts 50 may be positioned at various portions of ventilation interface 4, for example at the top and bottom of either side face 4. In a further embodiment, the headgear may have female connectors that allow for the headgear to be securely fastened to male attachment posts 50. In a different embodiment, the headgear may have looped ends that securely fit around attachment posts 50. Additionally, any other known type of attachments or posts may be used to securely attach headgear to respiration assist mask 2 in such as manner as to provide for the comfort of a user and allow for an airtight seal to be formed between the face of a user and respiration assist mask 2.

Figure 2:
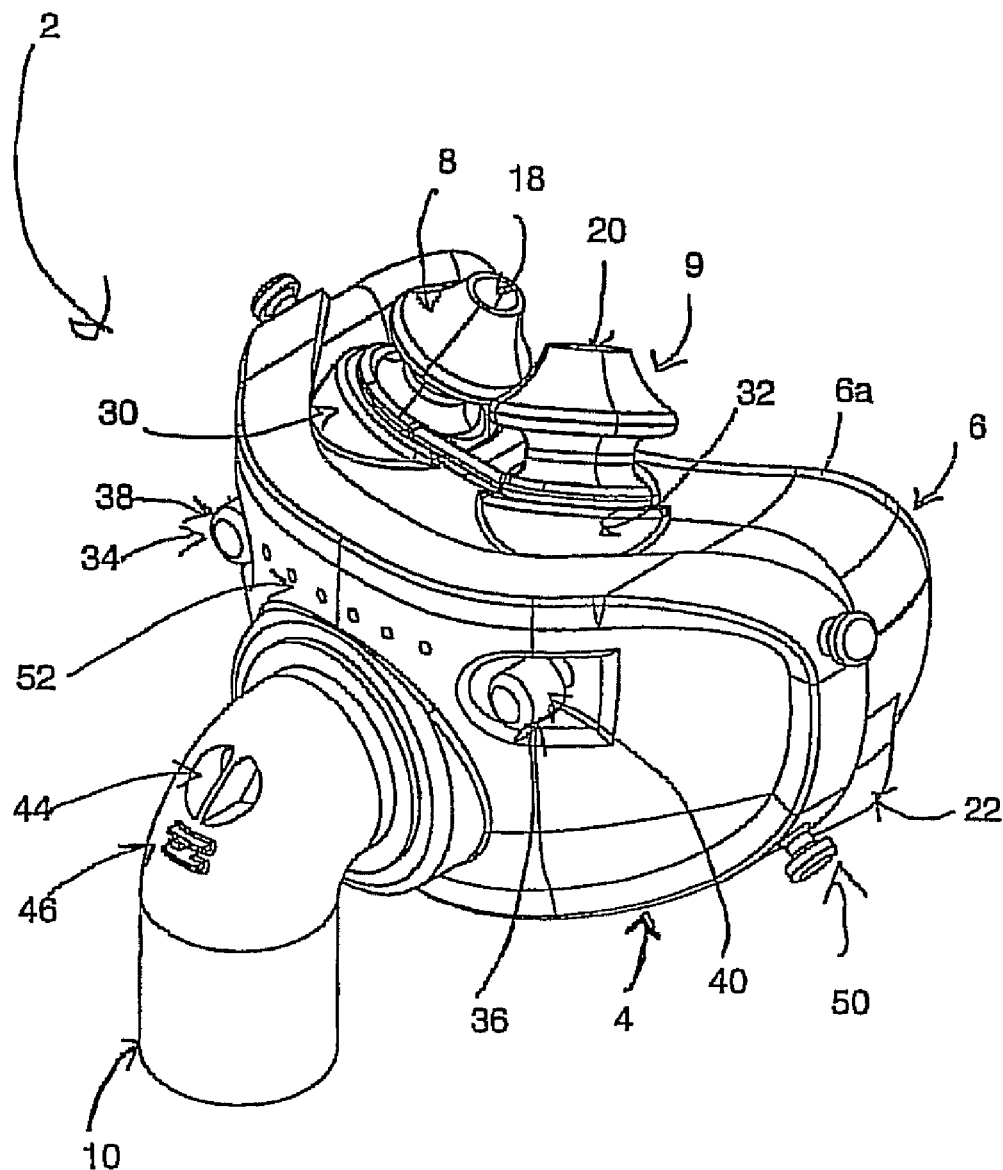
FIG. 2 shows a side perspective view of an exemplary embodiment of the invention.

FIG. 2 shows another exemplary embodiment where the components of the device are joined together. In this embodiment, gas input tube 10 may be securely connected to ventilation interface 4 through any of the methods mentioned previously. Additionally, tube 10 may be secured to face 4 to provide an airtight seal between the tube and the face, but it may be rotatably engaged to the face. Thus input gas tube 10 may be rotated so that a feed tube that may, optionally, be connected to input gas tube 10 can be mounted in any location or position and continue to supply input gas to respiration assist mask 2.

FIG. 2 also shows how ventilation interface 4 can be connected to facial interface 6. The mating of these two devices can create an airtight seal between face 4 and connector 6. Additionally, any known method of connecting the two components may be utilized, such as tongue in groove, clasps, clips or the like. Connector 6 may also serve to enhance the structural rigidity of respiration assist mask 2. For example, the top portion and side portions of connector 6 may be thicker than other portions of connector 6. This can allow for stabilization of nasal inserts 8 and 9 when they are joined with connector 6. Further, this may prevent fore and aft movement as well as lateral movement of nasal inserts 8 and 9 when they are joined with connector 6, and may also act to enhance the seal between the nasal inserts 8 and 9 and connector 6.

In a further embodiment shown in FIG. 2, nasal inserts 8 and 9 are shown connected to facial interface 6 through the use of receiving holes 12 and 14. This connection may also form an airtight seal between nasal inserts 8 and 9 and facial interface 6.

The assembled respiration assist mask 2 shown in FIG. 2 may be joined to provide airtight seals between each of the components. Additionally, when the device is positioned on the face of a user, an airtight seal may exist between the interior portion of respiration assist mask 2 and the face of the user.

In a further embodiment of the invention, exhaust ports 52 may be disposed on the face of respiration assist mask 2. In one exemplary embodiment, a series of exhaust ports 52 may be formed on the surface of ventilation interface 4. These ports 52 may be utilized to release or output carbon dioxide that is exhaled by a user wearing the mask. In an alternative embodiment, the exhaust ports may protrude from ventilation interface 4. In another embodiment, a different number of exhaust ports that may be larger or smaller may be utilized on ventilation interface 4. In yet another embodiment, one or more exhaust ports have adjustable apertures or adjustable flow rates may be disposed on ventilation interface 4. In still another embodiment, exhaust ports 52 may be capable of being capped or sealed from the interior or exterior of ventilation interface 4 so as to vary the flow rate of exhaust gases. In another exemplary embodiment, exhaust ports 52 may be disposed on any location of ventilation interface 4.

Figure 3:
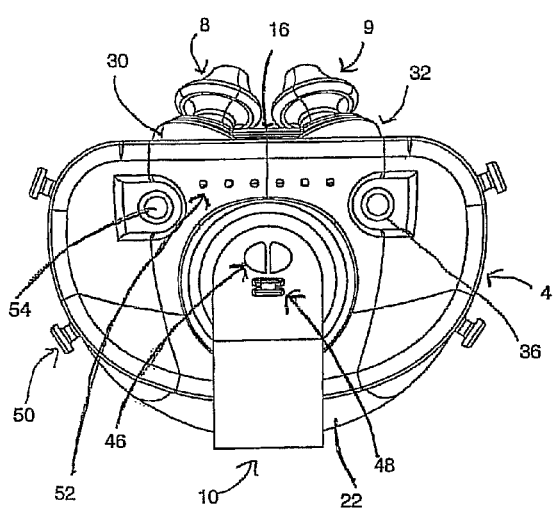
FIG. 3 shows a front view of an exemplary embodiment of the invention.
Figure 4:
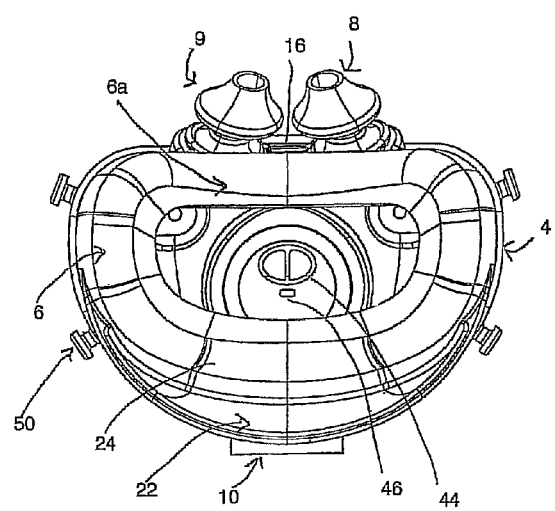
FIG. 4 shows a back view of an exemplary embodiment of the invention.

In a further embodiment shown in FIGS. 3 and 4, facial interface 6 may have an upper portion that is positioned against the upper lip of a user. For example, upper portion 6a of facial interface 6 may rest snugly against the upper lip of a user when respiration assist mask 2 is being worn. Upper portion 6a may act to create an airtight seal between the upper lip of a user wearing the device and connector 6. Additionally, upper portion 6a may act as an anchor portion for respiration assist mask 2 when it is being worn by a user. Thus if a user, for example, opens their mouth and moves their lower jaw while wearing the device, upper portion 6a of connector 6 will anchor respiration assist mask 2 on the face of the user to prevent it from being dislodged, which could potentially cause a break in the airtight seal between respiration assist mask 2 and the face of a user. Further, when upper portion 6a acts as an anchor, it may prevent forces on chin flap 22 caused by jaw or mouth movement of a user wearing the device from affecting the positioning and sealing of nasal inserts 8 and 9, which may be inserted into the nares of a user wearing the device. In this embodiment, stress exerted elsewhere on respiration assist mask 2 will not be translated into movement of nasal inserts 8 and 9 within the nares of a user and can prevent the dislodging of the nasal inserts from the nares.

In another embodiment of the invention shown in FIG. 4, upper portion 6a may also prevent movement of nasal inserts 8 and 9 when respiration assist mask 2 is worn or adjusted by a user. For example, if respiration assist mask 2 is worn on the face of a user through the use of headgear attached to posts 50, the user will likely need or desire to adjust the headgear so as to have comfort while ensuring the device is positioned properly. In previous devices having nasal inserts, the tightening of headgear on the head of a user would likely cause articulation and movement apart of the nasal inserts as the device onto which the nasal inserts was mounted stretched as the headgear was tightened. This articulation and movement can cause discomfort for a user and may dislodge the nasal inserts from the nares of a user. In this embodiment, however, upper portion 6a of connector 6 acts as an anchor for respiration assist mask 2 because it is positioned against the upper lip of a wearer to create a seal. Therefore any forces acting upon respiration assist mask 2 by the use or tightening of headgear will be absorbed by upper portion 6a of connector 6, rather than by nasal inserts 8 and 9. Thus, the comfort of a user wearing the device can be enhanced and there is a reduced possibility of nasal inserts 8 and 9 being moved within the nares of a user or dislodged, causing a break in the seal.

FIG. 5 shows a top down view of another embodiment of the invention. In this embodiment, nasal inserts 8 and 9 are shown as being angled towards each other. In other embodiments, nasal inserts 8 and 9 may be angled or orientated differently depending on the fitting required or desired by a user. Additionally, hole 54 on nasal insert 8 and hole 56 on nasal insert 9 may be elliptical. Other sizes and shapes of the holes may be utilized depending on the application and wearer of ventilation interface 2.

FIG. 6 shows a bottom up view of a different embodiment of the invention. This embodiment provides a bottom perspective facial interface 6 and chin flap 22. Additionally, one example of the placement of attachment posts 50 is shown. FIG. 6 also demonstrates the seal and one possible way of joining facial interface 6 and ventilation interface 4 where facial interface 6 fits into ventilation interface 4 in a tongue-in-groove fashion.

Figure 7:
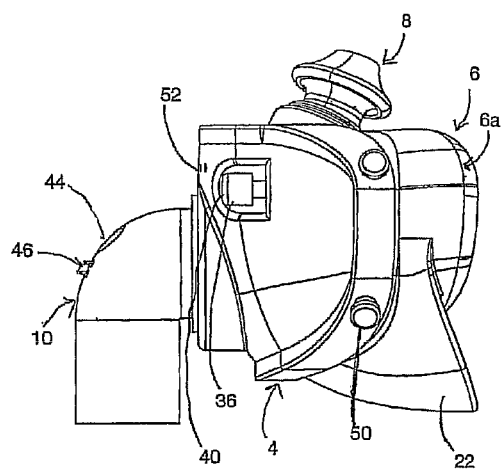
FIG. 7 shows a right side view of an exemplary embodiment of the invention.
Figure 8:
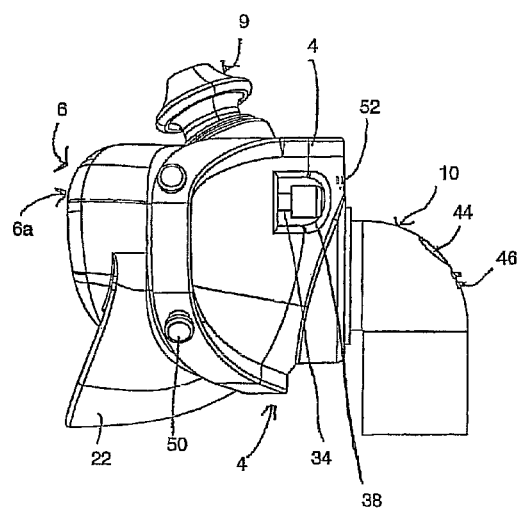
FIG. 8 shows a left side view of an exemplary embodiment of the invention.
Figure 9:
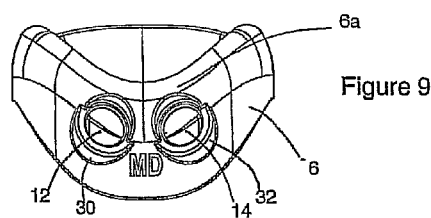
FIG. 9 shows a top-down view of an exemplary embodiment of the invention.
Figure 10:
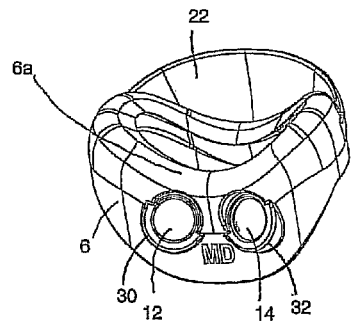
FIG. 10 shows a rotated top-down view of an exemplary embodiment of the invention.

FIGS. 7 and 8 show exemplary side views of the invention. In this embodiment, chin flap 22 on facial interface 6 extends beyond other portions of facial interface 6. Additionally, interface connector may have shaped edges which can contour to the face of a user to better provide a seal against the face of the user. FIGS. 7 and 8 also show auxiliary ports 34 and 36 as being disposed inside recessed or cut out portions of ventilation interface 4. In other embodiments of the invention, auxiliary ports 34 and 36 may be disposed in an area on ventilation interface 4 that is not cut out or recessed.

FIGS. 9-22 show an exemplary embodiment of cushioned facial interface 6. In this embodiment various membranes are shown as well as the difference between membranes. For example, the facial interface shown in FIGS. 9-15 may be smaller than the facial interface shown in FIGS. 16-22. Despite any size differences in the facial interfaces, both may be used interchangeably with ventilation interface 2 and nasal inserts 8 and 9 without any alterations to those devices. Additionally, as shown in FIGS. 14-15 and 21-22, membrane 24*a* is shown as an outer membrane that is thinner than inner membrane 24*b*. As discussed previously, membrane 24*a* can be made of any suitable material, such as silicone. As discussed above, membrane 24*a* is thin so as to be able to follow the contours of a user's face and provide a seal between facial interface 6 and the face of the user. Moreover, the thin membrane may be able to stretch in order to maintain a seal when the user's face moves, for example, such as when the user opens their mouth. Membrane 24*b* is shown as being thicker than membrane 24*a* and is also positioned inside membrane 24*a*. Membrane 24*b* may also be made out of any suitable material, such as silicone, and, as discussed above, may be thicker to provide support on the inside of mask 2. Membrane 24*b* may also serve to act as a "stop." In other words, membrane 24*b* may limit the amount of movement a user may have while wearing the mask, for example, preventing the user from opening their mouth beyond a certain point.

Figure 11:
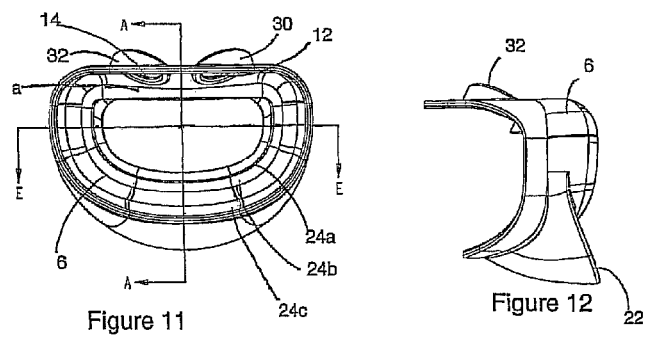
FIG. 11 shows a bottom-up view of an exemplary embodiment of the invention.
Figure 12:
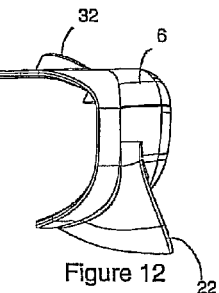
FIG. 12 shows a side view of an exemplary embodiment of the invention.
Figure 13:
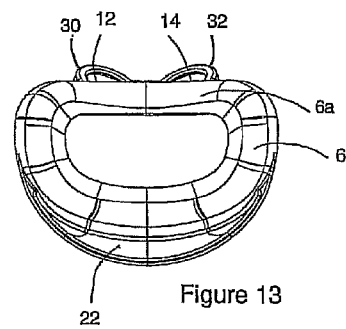
FIG. 13 shows a front view of an exemplary embodiment of the invention.
Figure 14:
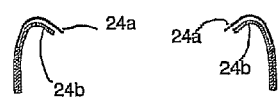
FIG. 14 shows cut out views of membranes in another exemplary embodiment of the invention.
Figure 15:
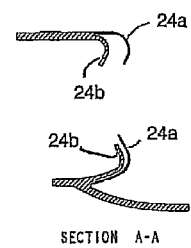
FIG. 15 shows cut out view of membranes in another exemplary embodiment of the invention.
Figure 16:
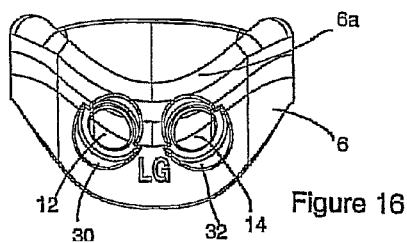
FIG. 16 shows a top-down view of an exemplary embodiment of the invention.
Figure 17:
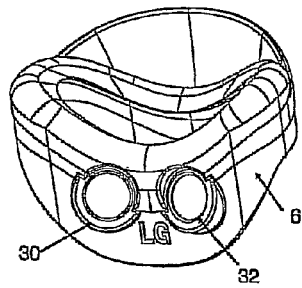
FIG. 17 shows a rotated top-down view of an exemplary embodiment of the invention.
Figure 18:
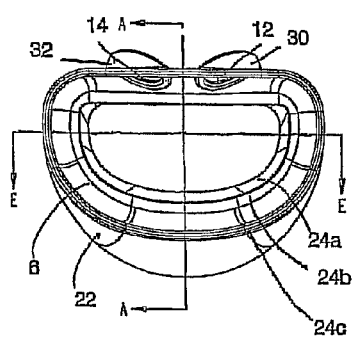
FIG. 18 shows a bottom-up view of an exemplary embodiment of the invention.
Figure 19:
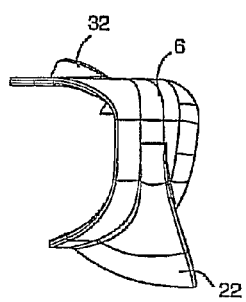
FIG. 19 shows a side view of an exemplary embodiment of the invention.
Figure 20:
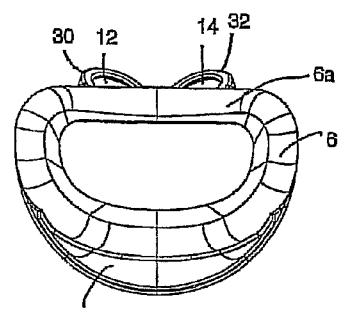
FIG. 20 shows a front view of an exemplary embodiment of the invention.
Figure 21:
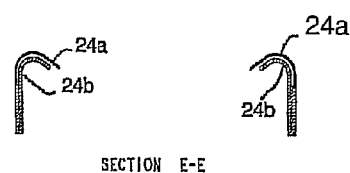
FIG. 21 shows cut out views of membranes in another exemplary embodiment of the invention.
Figure 22:
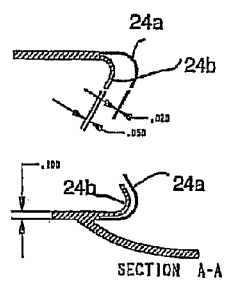
FIG. 22 shows cut out view of membranes in another exemplary embodiment of the invention.

Additionally, inner membrane 24*b* may be positioned adjacent membrane 24*a* such that a distance is defined therebetween. As shown in FIG. 11, the differences in the areas separating various membranes can be seen. As shown in FIGS. 11 and 18, the distance between membranes 24*a*, 24*b* and 24*c* is larger on axis A-A than it is on the E-E axis. The distance between membranes 24*a*-*c* on axis A-A can allow for increased user comfort and utility, as a seal can be made around the entire mouth of the user. Additionally, by having a seal around the entire mouth area, the structural rigidity of mask 2 can be increased. Further, because of the increased structural rigidity, a user may be able to tighten mask 2 on their face without causing flex in the central or peripheral portions of the mask which could lead to the seal between the user's face and the facial interface being broken. This membrane structure can also allow downward pressure to be exerted on nasal inserts 8 and 9 without dislodging nasal inserts 8 and/or 9 and without significantly deforming facial interface 6 so as to cause a break in the seal between the face of the user and facial interface 6.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed:

1. A respiration assist mask, comprising:
   a ventilation interface including a gas entry port defined in the ventilation interface;
   a positive gas pressure source tube coupled to the gas entry port of the ventilation interface to facilitate supplying a gas to the ventilation interface;
   a cushioned facial interface connected to said ventilation interface, the facial interface having a gas exit shaped to gas-tightly seal only the mouth from the environment, the cushioned facial interface comprising at least one first exterior membrane that facilitates providing a seal across an upper lip and around a mouth of a user, and at least one second interior membrane positioned adjacent the at least one first exterior membrane such that a distance is defined therebetween, wherein the entire portion of the at least one first exterior membrane that facilitates providing a seal across an upper lip of a user has a first edge that extends toward the gas exit shaped to gas-tightly seal only the mouth that does not extend further than an adjacent second edge of the at least one second interior membrane;
   at least one removable nasal insert removably coupled in flow communication to an orifice in an upper portion of the cushioned facial interface; and
   a cavity defined within the cushioned facial interface between the gas entry port and an end of the at least one removable nasal insert farthest from the cushioned facial interface.

2. The respiration assist mask of claim 1, wherein the cushioned facial interface further comprises an elongated portion at the bottom portion of the interface that extends away therefrom, the elongated portion facilitates at least one of providing a seal under a chin of the user and preventing movement of a lower jaw of the user.

3. The respiration assist mask of claim 1, wherein the at least one removable nasal insert is coupled with a second nasal insert.

4. The respiration assist mask of claim 1, further comprising at least one protrusion for the attachment of headgear.

5. The respiration assist mask of claim 1, wherein the ventilation interface and the cushioned facial interface are removably attached.

6. The respiration assist mask of claim 1, wherein the at least one first exterior membrane facilitates providing a seal and the at least one second interior membrane facilitates providing support to the at least one first exterior membrane.

7. The respiration assist mask of claim 1, wherein the at least one first exterior membrane facilitates providing a gas tight seal against the face of a user and the at least one second interior membrane being thicker than the at least one first exterior membrane and providing structural rigidity to the facial interface and limiting movement of the respiration assist mask.

8. The respiration assist mask of claim 7, wherein the distance between the at least one first exterior membrane and the at least one second interior membrane is larger at least one of a top portion and a bottom portion of the cushioned facial interface than the distance between the at least one first exterior membrane and the at least one second interior membrane at least one of a first side portion and a second side portion of the cushioned facial interface.

9. A respiration assist mask, comprising:
   a gas supply tube;
   a ventilation interface;
   a cushioned facial interface comprising a first exterior membrane that facilitates providing a seal across an upper lip and around a mouth of a user, and a second interior membrane positioned adjacent the first exterior membrane such that a distance is defined therebetween, wherein the entire portion of the at least one first exterior membrane that facilitates providing a seal across an upper lip of a user has a first edge that extends toward a gas exit shaped to gas-tightly seal only the mouth that does not extend further than an adjacent second edge of the at least one second interior membrane;

at least one nasal insert;

a cavity defined within the cushioned facial interface between the ventilation interface and an end of the at least one nasal insert farthest from the cushioned facial interface; and the gas supply tube removably connected to the ventilation interface and creating a seal therebetween, the cushioned facial interface removably connected to the ventilation interface and creating a seal therebetween, and the at least one nasal insert removably connected to an upper portion of the cushioned facial interface and creating a seal therebetween.

10. The respiration assist mask of claim 9, wherein the cushioned facial interface creates a first seal between the cushioned facial interface and an upper lip of a user and a second seal between the cushioned facial interface and a chin of a user.

11. The respiration assist mask of claim 9, wherein the at least one nasal insert is joined to a second nasal insert.

12. The respiration assist mask of claim 9, wherein the first exterior membrane is thinner than the second interior membrane.

13. The respiration assist mask of claim 9, wherein the first exterior membrane being separated from the second interior membrane by a greater distance at least one of a top portion and a bottom portion of the cushioned facial interface than at least one of a first side portion and a second side portion of the cushioned facial interface.

14. The respiration assist mask of claim 9, wherein the ventilation interface further comprises at least one protrusion for the attachment of head gear.

15. The respiration assist mask of claim 9, wherein the ventilation interface has at least one exhaust port defined therein.

16. A respiration assist mask of claim 1, wherein the ventilation interface comprises at least one exhalation port defined therein.

17. A respiration assist mask of claim 1, wherein the distance between the at least one first exterior membrane and the at least one second interior membrane is larger at a top portion of the cushioned facial interface than the distance between the at least one first exterior membrane and the at least one second interior membrane at least one of a bottom portion, a first side portion and a second side portion of the cushioned facial interface.

18. A respiration assist mask of claim 9, wherein the first exterior membrane being separated from the second interior membrane by a greater distance at a top portion of the cushioned facial interface than at least one of a bottom portion, a first side portion and a second side portion of the cushioned facial interface.

19. The respiration assist mask of claim 1, wherein the at least one first exterior membrane has a periphery edge at the gas exit that is configured to not contact the nose during use.

20. A respiration assist mask of claim 9, wherein the cushioned facial interface has a gas exit shaped to gas-tightly seal only the mouth from the environment, and wherein the first exterior membrane has a periphery edge at the gas exit that is configured to not contact the nose during use.

* * * * *